United States Patent [19]

King et al.

[11] Patent Number: 4,897,789
[45] Date of Patent: Jan. 30, 1990

[54] ELECTRONIC DEVICE FOR AUTHENTICATING AND VERIFYING DISPOSABLE ELEMENTS

[75] Inventors: Martin J. King, Seminole; Vernon H. Troutner, St. Petersburg, both of Fla.

[73] Assignee: McNeilab, Inc., Spring House, Pa.

[21] Appl. No.: 834,293

[22] Filed: Feb. 27, 1986

[51] Int. Cl.⁴ .............................................. G06F 15/42
[52] U.S. Cl. .................................... 364/413.07; 604/6; 604/4
[58] Field of Search ............ 364/415, 413, 29, 413.02, 364/413.07, 413.09; 390/679; 604/4, 153, 4, 6, 20, 21; 128/362

[56] References Cited

U.S. PATENT DOCUMENTS

| | | | |
|---|---|---|---|
| 4,493,706 | 1/1985 | Borsanyi | 604/153 |
| 4,537,561 | 8/1985 | Xanthopoulous | 128/DIG. 12 |
| 4,550,370 | 10/1985 | Baker | 364/413 |
| 4,568,328 | 2/1986 | King | 604/6 |
| 4,573,960 | 3/1986 | Goss | 604/6 |
| 4,573,961 | 3/1986 | King | 604/6 |
| 4,588,880 | 5/1986 | Hesser | 364/478 |
| 4,592,018 | 5/1986 | Wiegman | 128/672 |
| 4,611,601 | 9/1986 | Bowman | 128/673 |
| 4,613,937 | 9/1986 | Batty | 364/413 |
| 4,642,769 | 2/1987 | Petrofsky | 364/413 |
| 4,657,490 | 4/1987 | Abbott | 604/153 |
| 4,705,498 | 11/1987 | Goss | 604/6 |
| 4,756,706 | 7/1988 | Kerns et al. | 364/413.02 |
| 4,817,044 | 5/1989 | Ogren | 364/413.02 |

*Primary Examiner*—Jerry Smith
*Assistant Examiner*—Gail O. Hayes
*Attorney, Agent, or Firm*—Richard J. Grochala

[57] ABSTRACT

Authentication and verification of suitability for use of disposable elements can be made by evaluation of characteristic data stored on a non-volatile read/write memory element, especially useful in a photoactivatable agent patient treatment system wherein photoactivatable agents, in contact with patient blood cells, are irradiated extracorporeally and then returned to the patient.

8 Claims, 1 Drawing Sheet

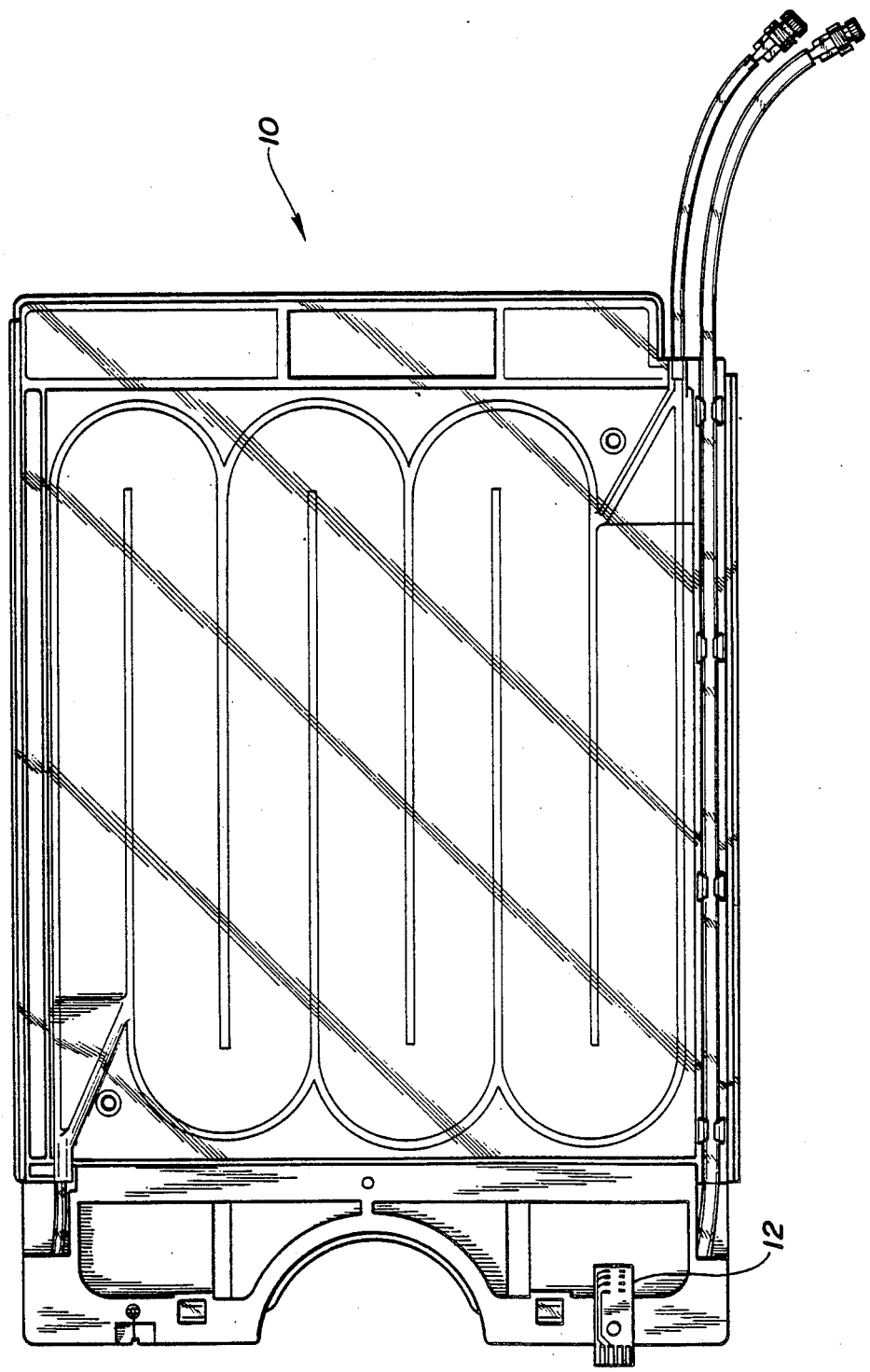

ELECTRONIC DEVICE FOR AUTHENTICATING AND VERIFYING DISPOSABLE ELEMENTS

FIELD OF THE INVENTION

This invention relates to the field of controlling the use of disposable elements and is especially useful for authenticating and verifying suitability of disposable elements for clinically useful systems for treating cells with photoactivatable compounds and radiation which activates the compound thereby affecting the cells such as for the extracorporeal treatment of blood cells, especially leukocytes, with UV radiation.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems require solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602, describes a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to U.S. Ser. No. 650,602.

To be fully practical, the Taylor device requires a clinically acceptable instrument to house the device and to provide the cells to be treated in an appropriate form. Such an instrument is the object of the inventions described in U.S. Pat. Nos. 4,573,960, 4,568,328, 4,578,056, 4,573,961, 4,596,547, 4,623,328, and 4,513,962, fully incorporated herein by reference. While the instruments described therein work well, it is an object of the instant application to describe improved systems capable of implementing, in advanced fashion, the medical treatment principles first taught by Edelson.

It is another object of the present invention to provide still further improvements in greater patient safety and comfort while reducing treatment time and cost, by utilizing newly designed disposable irradiation chambers and light array assemblies in a patient treatment instrument.

It is yet another object to provide an improved instrument which meets the above criteria along with all the positive attributes of the prior system; compactness, mobility, completeness, fully automated and monitored, and ease of operation.

It is a further related object of this invention to provide in contrast to the time consuming batch like processing of the prior system, continuous on-line patient treatment wherein collection, separation, and cell treatment occur simultaneously, thereby reducing treatment time and increasing patient safety and comfort.

It is still a further object to provide improved methods for monitoring the use of disposables including methods to authenticate a disposable prior to its initial use and to monitor its services and prevent overuse.

BRIEF DESCRIPTION OF THE DRAWING

The drawing depicts a rear elevational view of one embodiment of the combination of the present invention. The drawing shows a disposable flat plate irradiation chamber (10) which has permanently mounted thereto an integrated circuit mounted on a circuit board (12).

SUMMARY OF THE INVENTION

In accordance with the principles and objects of the present invention there are provided electronic means to authenticate and verify the suitability of the disposable elements for use and for monitoring the service time of such disposable for preventing overuse. The invention is especially useful with apparatus for "on-line" extracorporeally photoactivating a photoactivatable agent in contact with blood cells. Such a patient treatment apparatus collects and separates, on a continuous basis, blood from a patient while the patient is connected to the apparatus, returning undesired blood portions obtained during separation while photoactivating desired portions and thereafter returning thusly treated cells to the patient. As a result of this novel approach, the patient treatment systems optimize and minimize treatment time by concurrently conducting various aspects of such photoactivation treatment which were previously performed sequentially. Such a patient treatment system preferably utilizes two different disposable treatment elements comprising an irradiation chamber for containing the patient cells/fluid for exposure to photoactivating irradiation, and a light array assembly for providing the activating irradiation. The instant invention, while having broad applicability, is especially useful for authenticating these treatment elements prior to use and, in the case of the light array assembly, for monitoring the length of service to prevent use beyond the service life. The most preferred embodiment of the present invention comprises an electronic memory element which contains information characteristic to the treatment element in question. The memory element, typically an integrated circuit (IC), has associated contact points for electronic connection to, and communication with the apparatus for which the disposable is intended. Upon installation of the disposable into the apparatus, electrical contact is made with the memory IC and permits the apparatus to verify the disposable is in appropriate condition for use. Inappropriate, counterfeit, improper use can then be avoided by suitably programming the apparatus not to operate in those circumstances. A most preferred embodiment of the memory IC will be an electrically erasable programmable read only memory (EEPROM) which will be capable of receiving information from the apparatus thereby allowing interaction therebetween and thus monitoring of the service life of the disposable to prevent overuse. It will be recognized that the instant invention will serve to increase patient safety by ensuring that disposable treatment elements, meeting critically determined operating parameters are used and not readily circumvented by unproven, potentially failure prone and therefore hazardous disposable element copies.

DETAILED DESCRIPTION

The system developed for extracorporeally treating a patient are the result of a number of separate inventions some of which form the subject matter of previously described issued patents and copending commonly assigned applications including U.S. Ser. No. 834,292 entitled "Concurrent On-Line Irradiation Treatment Process"; U.S. Ser. No. 834,294 entitled "Disposable Temperature Probe For Photoactivation Patient Treatment System"; U.S. Pat. No. 4,681,568 entitled "Improved Valve Apparatus For Photoactivation Patient Treatment System"; U.S. Ser. No. 834,256 entitled "Light Array Assembly For Photoactivation Patient Treatment System"; U.S. Pat. No. 4,692,438 entitled "Pump Block For Interfacing Irradiation Chamber to Photoactivation Patient Treatment System"; U.S. Ser. No. 834,260 entitled "Demountable Peristaltic Pump For Photoactivation Patient Treatment System"; U.S. Pat. No. 4,687,464 entitled "Zero Insertion Force Socket For Photoactivation Patient Treatment System"; and U.S. Ser. No. 834,258 entitled "Irradiation Chamber For Photoactivation Patient Treatment System", the relevant parts of which are fully incorporated herein by reference. While a brief description of that patient treatment system may prove helpful to understand the nature of the disposable treatment elements used therein, it will be readily understood that the instant invention is not so limited.

The operation of the device and performance of the methods can be divided into two basic phases or modes. The first phase occurs when the patient is connected to the treatment apparatus by venipuncture or the like methods well-known and developed to a high degree in the dialysis arts. Patient blood, as it flows to the apparatus is preferably infused with an anticoagulant agent. Control of the flow of patient blood throughout the apparatus is largely controlled by a series of clamps controlled by the central processing unit under software and operator interactive control.

Normally the blood flows by action of a peristaltic pump (preferably a roller pump such as that described in U.S. Pat. No. 4,487,558 to Troutner entitled "Improved Peristaltic Pump" and fully incorporated herein by reference) through tubing into a continuous centrifuge. This continuous centrifuge, available commercially from suppliers such as Dideco, Haemonetics and others, is preferably capable of continuously separating blood based on the differing densities of the individual blood components. "Continuously", as used herein means that, as blood flows into the centrifuge, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by directly viewing the uppermost portion of the centrifuge bowl through the centrifuge cover, can detect qualitatively when the centrifuge emits plasma (as opposed to priming solution), leukocyte enriched portions and the remainder, i.e., nonleukocyte enriched portions, including erythrocyte enriched portions. Based on the operator's observations, he or she enters via the control panel the identification of the individual blood portions as they are emitted from the centrifuge. In response to this information, the apparatus controls valve mechanisms to direct the leukocyte enriched portion and a predetermined volume of plasma into plasma-leukocyte enriched container while excess plasma, air, priming fluids, erythrocytes etc. are directed to a return container for reinfusion to the patient.

Once the centrifuge is no longer capable of further separation due to the attainment of its capacity, the operator directs that the bowl be emptied by suitable data key entry on the control panel and the fluid contents of the centrifuge are advantageously pumped into the return container. The foregoing steps may be repeated a number of times or cycles before the desired volume of leukocyte enriched blood and plasma is obtained for further treatment, in each instance the undesired portions being collected in the return container.

Between cycles, the fluids, including erythrocytes which have been pumped into the return container are gravity fed back to the patient through a drip infusion operation. It is preferred that gravity feed be employed rather than actively pumping the blood back to the patient in order to avoid potential pressurization problems at the infusion insertion site at the patient, and also to avoid foaming or other air related dangers.

The leukocyte enriched container is also connected via a tubing line to a disposable flat plate irradiation chamber located within the apparatus. The chamber has a return tubing line to the leukocyte enriched container so that the fluids can be recirculated by means of another peristaltic roller pump through the flat plate irradiation chamber.

The irradiation chamber disposable can assume a variety of mechanical configurations but, in its most preferred embodiment, possess a serpentine pathway dimensioned to provide a large surface area to volume ratio thereby exposing a predominant portion of the patient fluids to photoactivating radiation. The chamber is ideally constructed of a material which is substantially transparent to the particular photoactivating radiation, chosen based on the type of photoactivatable agent employed. The most preferred embodiment of the patient treatment system employs a disposable irradiation chamber which is adapted to be received between two rows of irradiation sources, the disposable light array assembly, and to receive activating radiation simultaneously on both sides of the irradiation chamber. Thus, when the irradiation chamber is filled with patient fluid/cells, the light array assembly which surrounds the chamber is energized to provide the activating illumination. During illumination the recirculation pump rotor recirculates the patient fluid from the container through the chamber between the energized light array and back to the container. After a predetermined level of photoactivation has been achieved, the light array assembly is deenergized, the patient cells are pumped to the return container and then reinfused back to the patient. Ideally, operation of the patient treatment apparatus is largely under the control of a software programmed, electronic central processing unit (CPU) but subject to operator input. The CPU monitors the clamps, pumps, and safety devices throughout the apparatus to ensure patient safety and treatment efficiency. The CPU also communicates with the IC memory elements associated with the disposable.

The disposable flat plate irradiation chamber treatment element and the disposable light array assembly are more fully described in copending applications Ser. No. 834,258 and U.S. Ser. No. 834,256, respectively, and incorporated herein by reference.

The foregoing described patient treatment methods depend in large measure upon the quality and construction of the disposable flat plate irradiation chamber and the disposable light array assembly for safe and effective medical treatment. In the instance of the flat plate chamber it is important that it be sterile and unused (and therefore uncontaminated with the presence of possibly incompatible tissue types), made of materials appropriate to transmit the wavelength of radiation being employed, and that it be structurally sound and thus not subject to operational failure. In the instance of the light array assembly it is advantageous that the lights are of such construction and operation that the radiation intensity, distribution, and wavelength are appropriate and certifiable for the intended application. Since radiation characteristics of the light array degrade with usage, monitoring service to prevent overuse and thus reduced treatment efficacy is also of paramount importance. Because it is likely that arrays of differing radiation characteristics will be used for differing medical treatments, ensuring proper array—system interaction is also highly desirable.

Thus, for safe and effective medical treatment, it is clear that the photopheresis patient treatment system ideally will receive information from the disposables to enable it to determine that (1) the flat plate irradiation chamber is new and unused, (2) the flat plate chamber was manufactured of proper construction by a certifiable source, (3) the light array assembly was manufactured using proper irradiation sources from a certifiable source, (4) the specific type of light array assembly, and (5) the total accumulated time of usage of the light array assembly. The IC memory device, individually associated with each disposable meets these needs of authentication and verification in the following manner.

Each disposable includes as a permanently mounted feature, a solid state memory device, which can be written to or read from by an electronic microprocessor such as the central control microprocessor of the patient treatment system. The memory device, typically an integrated circuit device (or element as sometimes used herein), is ideally non-volatile in that it can retain stored information indefinitely without requiring an electrical power source. Such a device is commercially available and is commonly known as an EEPROM available under the brand name NOVRAM from XICOR Inc., California. Electrical connections between the IC memory element and the central control microprocessor of the apparatus can be readily accomplished through "finger-type" contacts on a circuit board on which the IC memory element is mounted and electrically connected. Thus, upon installation of the disposable with the IC memory device, the finger contacts are inserted into an electrical plug in type socket such as is described in U.S. Pat. No. 4,687,464.

During manufacture of the disposable, the IC memory element is ideally encoded, in a known manner, by a computer with disposable specific characteristic data such as serial number, type, certification code, and, if applicable, maximum usage time. When installed in the apparatus, the central control microprocessor, with preprogrammed instructions regarding the manner of encoding, can decode the disposable characteristic information to verify authenticity and certification, determine type of disposable and adjust procedure accordingly. In applicable instances, it can also periodically decrement the available usage time so that the operator of the apparatus can be warned when the disposable's useful lifetime has expired. Optionally, one can program the apparatus using the disposable-IC memory device to reject an 'expired' disposable or prohibit further useage thereof.

It will be readily apparent that many types of information can be stored in the IC memory device to regulate the use of a disposable. Further, while examples of use of the instant invention have been provided with respect to its use in photoactivated patient treatment systems, innumerable applications are apparent. These include any instance where it is necessary or desirable to control the use of disposable elements and/or prevent the use of unauthorized disposable elements. Additionally, while a most preferred IC memory element has been described, other non-volatile read/write memory devices may be equally useful including for instance magnetic recording strips or even electronic chips which require power sources to maintain a memory. Obvious disadvantages with the latter include possible decreased shelf-life and increased expense incurred with additional components.

Upon study of the foregoing description, numerous alternatives may occur to the skilled artisan without departing from either the spirit or scope of the instant invention.

What is claimed is:

1. A combination for insertion into an apparatus having microprocessor means for controlling said apparatus, the combination comprising:
   (a) a disposable or replaceable medical device for use in the photoactivated treatment of patient body fluids; and
   (b) an integrated circuit permanently mounted to the medical device, wherein the circuit has a non-volatile electronic memory having encoded data pertinent to the use of the disposable or replaceable medical device and is capable of electrical connection with said microprocessor means when inserted into said apparatus.

2. The combination of claim 1 wherein said data is selected from the group consisting of one or more of serial number, certification number, type, usage limitations, usage history, manufacture site, inspection or quality control related information, and performance criteria.

3. The combination of claim 1 wherein said memory means has read and write capability.

4. The combination of claim 1 wherein said disposable element is selected from the group consisting of an irradiation chamber, an irradiation cassette, a tubing set, a centrifuge bowl and a light array assembly.

5. The combination of claim 1 wherein said memory means is selected from the group consisting of an integrated circuit having a non-volatile memory, an integrated circuit and a power source for maintaining memory in said integrated circuit, and magnetic means for storing said data in the form of a magnetic memory.

6. The combination of claim 1, wherein the integrated circuit is mounted on a circuit board having electrical connections for electronic communication with the microprocessor means.

7. The combination of claim 1, wherein the integrated circuit has an electrically erasable programmable read only memory.

8. A method for authenticating and verifying the suitability of a disposable or replaceable medical device for use with an apparatus having microprocessor means for controlling said apparatus, the method comprising:
   (a) providing the combination of claim 1;
   (b) providing an apparatus having microprocessor means for controlling the apparatus, which has preprogrammed instructions regarding the data pertinent to the use of the disposable or replaceable medical device and is capable of decoding the data encoded in the integrated circuit memory; and
   (c) inserting the combination into the apparatus so that the integrated circuit electrically connects with the microprocessor and the microprocessor decodes the data encoded in the memory of the circuit, thereby authenticating and verifying the suitability of the disposable or replaceable medical device for use with the apparatus.

* * * * *